(12) United States Patent
Ito

(10) Patent No.: US 7,272,206 B2
(45) Date of Patent: Sep. 18, 2007

(54) METHOD AND APPARATUS FOR VOID CONTENT MEASUREMENT AND METHOD AND APPARATUS FOR PARTICLE CONTENT MEASUREMENT

(75) Inventor: Yoshiyasu Ito, Ome (JP)

(73) Assignee: Rigaku Corporation, Tokyo (JP)

( * ) Notice: Subject to any disclaimer, the term of this patent is extended or adjusted under 35 U.S.C. 154(b) by 84 days.

(21) Appl. No.: 11/072,924

(22) Filed: Mar. 4, 2005

(65) Prior Publication Data
US 2005/0195940 A1   Sep. 8, 2005

(30) Foreign Application Priority Data
Mar. 4, 2004   (JP) .............................. 2004-061358

(51) Int. Cl.
*G01B 15/02* (2006.01)
(52) U.S. Cl. .............................. 378/90; 378/58; 378/70
(58) Field of Classification Search ................. 378/70, 378/89, 90, 58
See application file for complete search history.

(56) References Cited

U.S. PATENT DOCUMENTS

| 6,895,075 B2 * | 5/2005 | Yokhin et al. ................. 378/90 |
| 7,116,755 B2 * | 10/2006 | Omote ......................... 378/86 |
| 2003/0157559 A1 | 8/2003 | Omote et al. |
| 2004/0066893 A1 | 4/2004 | Ito et al. |

FOREIGN PATENT DOCUMENTS

| JP | 10-038821 A | 2/1998 |
| JP | 10-38821 A | 2/1998 |
| JP | 2001-349849 A | 12/2001 |
| JP | 2003-202305 A | 7/2003 |

OTHER PUBLICATIONS

Svergun D. I. Et al. "Solution scattering structural analysis of the 70's Excherichuia coli ribosome by contrast variation. II. A model of the ribosome and its RNA at 3.5 nm resolution" Journal of Molecular Biology, London, GB vol. 271, No. 4, Aug. 29, 1997, pp. 602-618, XP 004453720, ISN: 0022-2836.

* cited by examiner

*Primary Examiner*—Edward J. Glick
*Assistant Examiner*—Thomas R. Artman
(74) *Attorney, Agent, or Firm*—Frishauf, Holtz, Goodman & Chick, P.C.

(57) ABSTRACT

A void or particle content is determined using the X-ray small angle scattering measurement for a sample made of a thin film having voids or particles disorderly dispersed in the matrix, the diffraction peaks being not available for such a sample. The invention includes three aspects. The first aspect is that an equipment constant is determined and an unknown void or particle content is calculated based on the equipment constant. The second aspect is that a plurality of samples having unknown matrix densities are prepared, the matrix densities are determined so that differences in the matrix densities among the samples become a minimum, and a void or particle content is calculated based on the matrix density and the scale factor of the X-ray small angle scattering. The third aspect is for a plurality of samples having unknown particle densities, and executes procedures similar to those of the second aspect.

16 Claims, 23 Drawing Sheets

FIG. 2

$$\rho_F = p\, \rho_{pore} + (1-p)\, \rho_M \qquad (1)$$

$$p = 1 - (\rho_F / \rho_M) \qquad (2)$$

$$I = k_0 \frac{p}{1-p} r_e^2 \left| \frac{f_F}{M_F} \rho_F\, F(q, para) \right|^2 \qquad (3)$$

$$I = S\, r_e^2 \left| \frac{f_F}{M_F} \rho_F\, F(q, para) \right|^2 \qquad (4)$$

$$S = k_0 \frac{p}{1-p} \qquad (5)$$

$$k_0 = \frac{1-p}{p} S \qquad (6)$$

$$p = \frac{S}{k_0 + S} \qquad (7)$$

FIG. 3

$$I = k_0 \frac{p}{1-p} r_e^2 \left| \left[ \frac{f_F}{M_F} \rho_F - \frac{f_{par}}{M_{par}} \rho_{par} \right] F(q, para) \right|^2 \quad (8)$$

$$I = S r_e^2 \left| \left[ \frac{f_F}{M_F} \rho_F - \frac{f_{par}}{M_{par}} \rho_{par} \right] F(q, para) \right|^2 \quad (9)$$

$$p_i = 1 - (\rho_{Fi} / \rho_{Mi}), \quad i = 0, 1, 2, 3 \cdots \quad (10)$$

$$I^{(i)} = k_0 \frac{p_i}{1-p_i} r_e^2 \left| \frac{f_{Fi}}{M_{Fi}} \rho_{Fi} F(q, para^{(i)}) \right|^2 \quad (11)$$

$$I^{(i)} = S_i r_e^2 \left| \frac{f_{Fi}}{M_{Fi}} \rho_{Fi} F(q, para^{(i)}) \right|^2 \quad (12)$$

$$S_i = k_0 \frac{p_i}{1-p_i} \quad (13)$$

$$k_0 = \frac{1-p_0}{p_0} S_0 = \frac{1-p_1}{p_1} S_1 = \frac{1-p_2}{p_2} S_2 = \cdots \quad (14)$$

FIG. 4

$$k_0 = \frac{\rho_{F0}}{\rho_{M0} - \rho_{F0}} S_0 = \frac{\rho_{F1}}{\rho_{M1} - \rho_{F1}} S_1$$

$$= \frac{\rho_{F2}}{\rho_{M2} - \rho_{F2}} S_2 = \frac{\rho_{F3}}{\rho_{M3} - \rho_{F3}} S_3 = \cdots \quad (15)$$

$$p_1 = \frac{1}{1 + \frac{S_0}{S_1} \frac{1 - p_0}{p_0}}, \quad p_2 = \frac{1}{1 + \frac{S_0}{S_2} \frac{1 - p_0}{p_0}},$$

$$p_3 = \frac{1}{1 + \frac{S_0}{S_3} \frac{1 - p_0}{p_0}}, \quad \cdots \quad (16)$$

$$\rho_{M1} = \rho_{F1} + \frac{\rho_{F1}}{\rho_{F0}} \frac{S_1}{S_0} (\rho_{M0} - \rho_{F0}),$$

$$\rho_{M2} = \rho_{F2} + \frac{\rho_{F2}}{\rho_{F0}} \frac{S_2}{S_0} (\rho_{M0} - \rho_{F0}),$$

$$\rho_{M3} = \rho_{F3} + \frac{\rho_{F3}}{\rho_{F0}} \frac{S_3}{S_0} (\rho_{M0} - \rho_{F0}), \quad \cdots \quad (17)$$

FIG. 5

$$\text{MinFun}(\rho_{M0}, \rho_{M1}, \rho_{M2}, \cdots) = \frac{\sqrt{\sum_i \sum_{j \neq i} (\rho_{Mi} - \rho_{Mj})^2}}{\sum_i \rho_{Mi}} \quad (18)$$

$$\frac{\partial \text{MinFun}(\rho_{M0})}{\partial \rho_{M0}} = \frac{\partial}{\partial \rho_{M0}} \frac{\sqrt{\sum_i \sum_{j \neq i} (\rho_{Mi}(\rho_{M0}) - \rho_{Mj}(\rho_{M0}))^2}}{\sum_i \rho_{Mi}(\rho_{M0})} = 0 \quad (19)$$

$$\rho_{M0} = \frac{\text{Numerator}}{\text{Denominator}} \quad (20)$$

Numerator
$$= \rho_{F0}((S_0 - S_1)^2 \rho_{F0} \rho_{F1}^2 - (S_0 - S_1)(S_1 - S_2) \rho_{F1}^2 \rho_{F2}$$
$$+ (S_0 - S_2)(S_0 \rho_{F0} + S_1 \rho_{F1} - S_2(\rho_{F0} + \rho_{F1})) \rho_{F2}^2)$$

Denominator
$$= S_2^2(\rho_{F0} + \rho_{F1}) \rho_{F2}^2 + S_1^2 \rho_{F1}^2 (\rho_{F0} + \rho_{F2})$$
$$+ S_0^2 (\rho_{F1} + \rho_{F2}) \rho_{F0}^2 - S_1 S_2 \rho_{F1} \rho_{F2} (\rho_{F1} + \rho_{F2})$$
$$- S_0 \rho_{F0}(S_1 \rho_{F1}(\rho_{F0} + \rho_{F1}) + S_2 \rho_{F2}(\rho_{F0} + \rho_{F2}))$$

FIG. 6

$$\rho_{M1} = \rho_{F1} + \frac{\rho_{F1} S_1}{\rho_{F0} S_0} (\rho_{M0} - \rho_{F0}) \qquad (21)$$

$$\rho_{M2} = \rho_{F2} + \frac{\rho_{F2} S_2}{\rho_{F0} S_0} (\rho_{M0} - \rho_{F0}) \qquad (22)$$

$$\rho_{M1} = \rho_{F1} + \frac{\rho_{F1} - \rho_{par1}}{\rho_{F0} - \rho_{par0}} \frac{S_1}{S_0} (\rho_{M0} - \rho_{F0}),$$

$$\rho_{M2} = \rho_{F2} + \frac{\rho_{F2} - \rho_{par2}}{\rho_{F0} - \rho_{par0}} \frac{S_2}{S_0} (\rho_{M0} - \rho_{F0}),$$

$$\rho_{M3} = \rho_{F3} + \frac{\rho_{F3} - \rho_{par3}}{\rho_{F0} - \rho_{par0}} \frac{S_3}{S_0} (\rho_{M0} - \rho_{F0}), \quad \cdots \qquad (23)$$

$$p = \frac{\rho_M - \rho_F}{\rho_M - \rho_{par}} \qquad (24)$$

FIG. 9

Parameters determined in the X-ray reflectance method

|  | Material | Density [g/cm$^3$] | Thickness [nm] | Roughness [nm] |
|---|---|---|---|---|
| Sample 0 | Si$_2$O$_3$C$_2$H$_6$ | $\rho_{F0}$ =1.165 | 405.08 | 1.55 |
|  | Si | 2.33 | - | 0.733 |
| Sample 1 | Si$_2$O$_3$C$_2$H$_6$ | $\rho_{F1}$ =1.078 | 402.95 | 1.56 |
|  | Si | 2.33 | - | 0.87 |
| Sample 2 | Si$_2$O$_3$C$_2$H$_6$ | $\rho_{F2}$ =0.994 | 398.54 | 1.53 |
|  | Si | 2.33 | - | 1.09 |

Profile fitting for the offset scanning in the X-ray small angle scattering measurement of sample 1

Profile fitting for the rocking scanning in the X-ray small angle scattering measurement of sample 1

FIG. 14

Parameters and scale factors determined
in the X-ray small angle scattering method

|  | Average diameter [nm] | Variance | Scale factor |
|---|---|---|---|
| Sample 0 | 2.45 | 0.74 | $S_0 = 0.854$ |
| Sample 1 | 2.11 | 0.55 | $S_1 = 1.255$ |
| Sample 2 | 2.22 | 0.48 | $S_2 = 1.695$ |

Relative matrix density on the basis of sample 0

FIG. 17

Values used for calculating void contents
and calculated void contents

| | Average density [g/cm$^3$] | Scale factor | Matrix density [g/cm$^3$] | Void content |
|---|---|---|---|---|
| Sample 0 | $\rho_{F0}$ =1.165 | $S_0$ =0.854 | $\rho_{M0}$ =1.412 | $p_0$ =0.175 |
| Sample 1 | $\rho_{F1}$ =1.078 | $S_1$ =1.255 | $\rho_{M1}$ =1.413 | $p_1$ =0.237 |
| Sample 2 | $\rho_{F2}$ =0.994 | $S_2$ =1.695 | $\rho_{M2}$ =1.412 | $p_2$ =0.296 |

FIG. 18

$$\left|F(q, para)\right|^2 = \left|F(q, D_0, \sigma)\right|^2$$

$$= \frac{1}{\frac{4\pi}{3}\left(\frac{D_0}{2}\right)^3} \int_0^\infty \left[\frac{4\pi}{q^3}\left(\sin\left(\frac{qD}{2}\right) - \frac{qD}{2}\cos\left(\frac{qD}{2}\right)\right)\right]^2$$

$$\times\ Q(D, D_0, \sigma)\frac{D_0^3}{D^3}\ dD \quad\quad (25)$$

$$\left|F(q, para)\right|^2 = \left|F(q, \xi)\right|^2 = \frac{8\pi\xi^3}{(1+q^2\xi^2)^2} \quad\quad (26)$$

FIG. 19

$$f = f_0 + f_1(q) + if_2(q) \doteq Z + f_1(q) + if_2(q) \quad (27)$$

Average atomic scattering factor $f_F$
and average atomic mass $M_F$

|  | $f_0 \doteq Z$ | $f_1$ (CuK$\alpha$) | $f_2$ (CuK$\alpha$) | Atomic mass M | Mole ratio |
|---|---|---|---|---|---|
| Si | 14 | 0.2436 | 0.3300 | 28.086 | 2 |
| O | 8 | 0.0464 | 0.0322 | 15.9994 | 3 |
| C | 6 | 0.0168 | 0.0090 | 12.01115 | 2 |
| H | 1 | 0.0000 | 0.0000 | 1.00797 | 6 |
| Avg | $f_F$ = 5.43538 + i 0.05958 | | | $M_F$ = 10.3257 | |

FIG. 20

$$I = k_0 \frac{1-p}{p} r_e^2 \left| \left( \frac{f_M}{M_M} \rho_M - \frac{f_F}{M_F} \rho_F \right) F(q, \text{para}) \right|^2 \quad (28)$$

$$I = S r_e^2 \left| \left( \frac{f_M}{M_M} \rho_M - \frac{f_F}{M_F} \rho_F \right) F(q, \text{para}) \right|^2 \quad (29)$$

$$S = k_0 \frac{1-p}{p} \quad (30)$$

$$k_0 = \frac{p}{1-p} S \quad (31)$$

$$p = \frac{k_0}{k_0 + S} \quad (32)$$

$$k_0 = \frac{p_0}{1-p_0} S_0 = \frac{p_1}{1-p_1} S_1 = \frac{p_2}{1-p_2} S_2 = \cdots \quad (33)$$

$$\rho_F = p \rho_{\text{par}} + (1-p) \rho_M \quad (34)$$

FIG. 21

$$k_0 = \frac{\rho_{M0} - \rho_{F0}}{\rho_{F0} - \rho_{par0}} S_0 = \frac{\rho_{M1} - \rho_{F1}}{\rho_{F1} - \rho_{par1}} S_1$$

$$= \frac{\rho_{M2} - \rho_{F2}}{\rho_{F2} - \rho_{par2}} S_2 = \frac{\rho_{M3} - \rho_{F3}}{\rho_{F3} - \rho_{par3}} S_3 = \cdots \quad (35)$$

$$\rho_{par1} = \rho_{F1} + \frac{\rho_{M1} - \rho_{F1}}{\rho_{M0} - \rho_{F0}} \frac{S_1}{S_0} (\rho_{par0} - \rho_{F0}),$$

$$\rho_{par2} = \rho_{F2} + \frac{\rho_{M2} - \rho_{F2}}{\rho_{M0} - \rho_{F0}} \frac{S_2}{S_0} (\rho_{par0} - \rho_{F0}),$$

$$\rho_{par3} = \rho_{F3} + \frac{\rho_{M3} - \rho_{F3}}{\rho_{M0} - \rho_{F0}} \frac{S_3}{S_0} (\rho_{par0} - \rho_{F0}), \quad \cdots \quad (36)$$

FIG. 22

$$I = I_a + I_b + I_c + I_d \qquad (37)$$

$$I_a = S\, r_e^2 \left| \frac{f_F}{M_F} \rho_F\, F(q_L^+) \right|^2 \left[ \frac{1 - e^{-2v_0 \operatorname{Im}(\alpha_L + \zeta_L)\, d_L}}{2 v_0 \operatorname{Im}(\alpha_L + \zeta_L)} \right] \qquad (38)$$

$$I_b = S\, r_e^2 \left| \frac{f_F}{M_F} \rho_F\, F(q_L^-) \right|^2$$

$$\times \left[ e^{-4v_0 \operatorname{Im}(\zeta_L)\, d_L} \cdot \frac{1 - e^{-2v_0 \operatorname{Im}(\alpha_L - \zeta_L)\, d_L}}{2 v_0 \operatorname{Im}(\alpha_L - \zeta_L)} \right] \qquad (39)$$

$$I_c = S\, r_e^2 \left| \frac{f_F}{M_F} \rho_F\, F(q_L^-) \right|^2$$

$$\times \left[ e^{-4v_0 \operatorname{Im}(\alpha_L)\, d_L} \cdot \frac{1 - e^{-2v_0 \operatorname{Im}(\zeta_L - \alpha_L)\, d_L}}{2 v_0 \operatorname{Im}(\zeta_L - \alpha_L)} \right] \qquad (40)$$

$$I_d = S\, r_e^2 \left| \frac{f_F}{M_F} \rho_F\, F(q_L^+) \right|^2$$

$$\times \left[ e^{-4v_0 \operatorname{Im}(\zeta_L + \alpha_L)\, d_L} \cdot \frac{e^{+2v_0 \operatorname{Im}(\alpha_L + \zeta_L)\, d_L} - 1}{2 v_0 \operatorname{Im}(\alpha_L + \zeta_L)} \right] \qquad (41)$$

FIG. 23

$$q_L^+ = v_0 \operatorname{Re}(\alpha_L + \zeta_L) \qquad (42)$$

$$q_L^- = v_0 \left| \operatorname{Re}(\alpha_L - \zeta_L) \right| \qquad (43)$$

$$v_0 = \frac{2\pi}{\lambda} \qquad (44)$$

$$\alpha_L = \sqrt{n_L^2 - \cos^2 \theta_0} \qquad (45)$$

$$\zeta_L = \sqrt{n_L^2 - \cos^2 \phi_0} \qquad (46)$$

METHOD AND APPARATUS FOR VOID CONTENT MEASUREMENT AND METHOD AND APPARATUS FOR PARTICLE CONTENT MEASUREMENT

BACKGROUND OF THE INVENTION

1. Field of the Invention

The present invention relates to a method and an apparatus for the measurement of a void content and a particle content with the use of the X-ray small angle scattering method.

2. Description of the Related Art

The present invention relates to the measurement of the void content or the particle content of a sample made of a thin film which has a matrix and voids or particles dispersed in the matrix. The matrix represents the base material in which voids or particles exist. FIGS. 1A and 1B are exemplary sectional views of the sample to which the present invention is applied. The sample shown in FIG. 1A is a thin film 10 on a substrate 18, the thin film 10 having a matrix 12 and voids 14 dispersed in the matrix 12. Thinking about the specific region of the thin film, a ratio of the total volume of the voids 14 existing in the region to the volume of the thin film in the region can be defined as a void content in the region. The sample shown in FIG. 1B is a thin film 10 having a matrix 12 and particles 16, whose material is different from the matrix, dispersed in the matrix 12. Similarly to the case having voids, thinking about the specific region of the thin film, a ratio of the total volume of the particles 16 existing in the region to the volume of the thin film in the region can be defined as a particle content in the region.

A technique of forming particles or voids with a nanometer size in a thin film gets a lot of attention in the recent development of the nanotechnology. The particles with a nanometer size are in the spotlight mainly in view of the improvement and variation of the properties caused by the quantum size effect. The voids with a nanometer size are expected to realize the porous interlayer insulation material in connection with the fine structure wiring of the semiconductor device. The particles or voids with a nanometer size can not be observed by the ordinary X-ray diffraction method because of the small periodicity. Therefore, the X-ray small angle scattering method and the EXAFS method would be important for observing the electron density fluctuation with a nanometer order. Especially, the X-ray small angle scattering method has been used from old times as the technique for evaluating the electron density fluctuation in a material with several nanometers to several hundred nanometers, for example, it has been used for the size evaluation of the particles or the voids and the evaluation of the long-period structure.

It is noted that the present invention relates to the measurement of the void content or the particle content of the sample with the use of the X-ray small angle scattering method, such a measurement is disclosed in Japanese patent publication No. 2001-349849 A, which will be referred to as the first publication. The first publication discloses the analysis of the thin film having voids or particles dispersed therein with the use of the X-ray small angle scattering method and the parameter fitting operation between the measured profile of the scattered intensity and the theoretical profile of the scattered intensity to determine the optimum values of the parameters. The embodiment of the first publication uses the scattering function for the theoretical profile of the scattered intensity, the function being a model in which the voids or the particles are assumed to be spherical or cylindrical and the size and its variance (which indicates the distribution of the size) are used as parameters to determine the size and the variance of the void or the particle. The first publication also discloses that a scattering function is produced using a void or particle content and its correlation distance as parameters, and a parameter fitting operation is carried out to determine the void or particle content and its correlation distance.

Formulae for determining the scattered X-ray intensity in connection with a thin film having voids or particles are disclosed in Japanese patent publication No. 2003-202305 A, which will be referred to as the second publication.

It is noted that the embodiment of the present invention carries out the measurement of the average density and the film thickness of the thin film using the X-ray reflectance method as the preliminary step before producing the theoretical profile of the X-ray small angle scattering, the measurement of the average density and the film thickness of the thin film using the X-ray reflectance method is known and disclosed in, for example, Japanese patent publication No. 10-38821 A (1998), which will be referred to as the third publication.

Although the prior art disclosed in the first publication can measure the void or particle content using the X-ray small angle scattering method, the prior art has the problems described below. The method disclosed in the first publication uses a model in which the analysis is effective in the case that the proximal distance of the voids or particles is held at a certain distance, i.e., the state of the short-range-order. When the proximal distance of the voids or particles is held at a certain distance, a diffraction peak corresponding to the distance can be observed on the X-ray small angle scattering pattern. The proximal distance of the voids or particles and the void or particle content can be evaluated based on the appearance angle of the diffraction peak, which corresponds to the proximal distance, and the spread of the diffraction peak, which is evaluated with the full-width-at-half-maximum and corresponds to the void or particle content. This method is effective only in the case that the proximal distance is held at a certain distance and thus is not applicable to a system in which voids or particles are randomly dispersed.

SUMMARY OF THE INVENTION

It is an object of the present invention to provide a method and an apparatus for measurement which can determine a void content or a particle content with the use of the X-ray small angle scattering method even when the diffraction peak can not be observed.

The present invention discloses three aspects. The first aspect is as follows. An equipment constant of the X-ray small angle scattering equipment is determined for a sample having a known void or particle content. Unknown void or particle content of another sample is calculated using the equipment constant.

The second aspect is as follows. There are prepared a plurality of samples which have unknown matrix densities expected to be identical with each other and void or particle contents expected to be different from each other. The scale factor of the X-ray small angle scattering is determined for each of the samples. The matrix density of each of the samples is determined using the scale factors under the provision that "the difference in matrix density among the samples becomes a minimum". The void or particle content is calculated based on the determined matrix densities and the scale factors. In measuring the void content according to the second aspect, the particle density should be known.

The third aspect is as follows. There are prepared a plurality of samples made of thin films which have known matrix densities, unknown particle densities expected to be identical with each other, and particle contents expected to be different from each other. The scale factor of the X-ray small angle scattering is determined for each of the samples. The particle density of each of the samples is determined using the scale factors under the provision that "the difference in particle density among the samples becomes a minimum". The particle content is calculated based on the determined particle densities and the scale factors.

Any aspect of the invention utilizes the scale factor, which expresses the absolute value of the X-ray small angle scattering, as an important element and the void or particle content is calculated based on the scale factor. The three aspects of the invention are common to each other in the viewpoint of the use of the scale factor.

The claims of the present patent application include twelve independent claims which will be explained in brief.

Claims 1 to 6 relate to the first aspect. The invention of claim 1 is an invention of a method in which the first aspect is applied to the void content measurement, and the invention of claim 2 is an invention of an apparatus corresponding to the invention of claim 1. The invention of claim 3 is an invention of a method in which the first aspect is applied to the particle content measurement in the case of the known particle density, and the invention of claim 4 is an invention of an apparatus corresponding to the invention of claim 3. The invention of claim 5 is an invention of a method in which the first aspect is applied to the particle content measurement in the case of the known matrix density, and the invention of claim 6 is an invention of an apparatus corresponding to the invention of claim 5.

Claims 7 to 14 relate to the second aspect. The invention of claim 7 is an invention of a method in which the second aspect is applied to the void content measurement, and the invention of claim 11 is an invention of an apparatus corresponding to the invention of claim 7. The invention of claim 12 is an invention of a method in which the first aspect is applied to the particle content measurement, and the invention of claim 14 is an invention of an apparatus corresponding to the invention of claim 12.

Claims 15 and 16 relate to the third aspect. The invention of claim 15 is an invention of a method regarding the third aspect, and the invention of claim 16 is an invention of an apparatus corresponding to the invention of claim 15.

The present invention has the advantages described below. The void or particle content can be determined with the use of the X-ray small angle scattering measurement even when the voids or particles are randomly dispersed and thus the diffraction peaks can not be observed. With the use of the first aspect, the equipment constant can be calculated using samples having known void or particle contents, and thereafter unknown void or particle contents can be determined using the equipment constant. With the use of the second and the third aspects, the equipment constant can be determined using samples having different void or particle contents even without a sample having a known void or particle content, and thereafter unknown void or particle contents can be determined using the equipment constant.

BRIEF DESCRIPTION OF THE DRAWINGS

FIG. 2 shows formulae (1) to (7) in connection with calculation of a void content or a particle content;
FIG. 3 shows formulae (8) to (14) in connection with calculation of a void content or a particle content;
FIG. 4 shows formulae (15) to (17) in connection with calculation of a void content or a particle content;
FIG. 5 shows formulae (18) to (20) in connection with calculation of a void content or a particle content;
FIG. 6 shows formulae (21) to (24) in connection with calculation of a void content or a particle content;
FIG. 9 shows a table indicating parameters determined in the X-ray reflectance method;
FIG. 14 shows a table indicating parameters and scale factors determined in the X-ray small angle scattering method;
FIG. 17 shows a table indicating values used for calculating void contents and calculated void contents;
FIG. 18 shows formulae (25) and (26) expressing scattering functions;
FIG. 19 shows a formula (27) expressing atomic scattering factor and a table indicating an example of calculation for the average atomic scattering factor and the average atomic mass;
FIG. 20 shows formulae (28) to (34) in connection with calculation of a void content or a particle content;
FIG. 21 shows formulae (35) and (36) in connection with calculation of a void content or a particle content;
FIG. 22 shows formulae (37) to (41) in connection with calculation of a void content or a particle content;
and
FIG. 23 shows formulae (42) to (46) in connection with calculation of a void content or a particle content.

DETAILED DESCRIPTION OF THE PREFERRED EMBODIMENTS

Figure 1A:
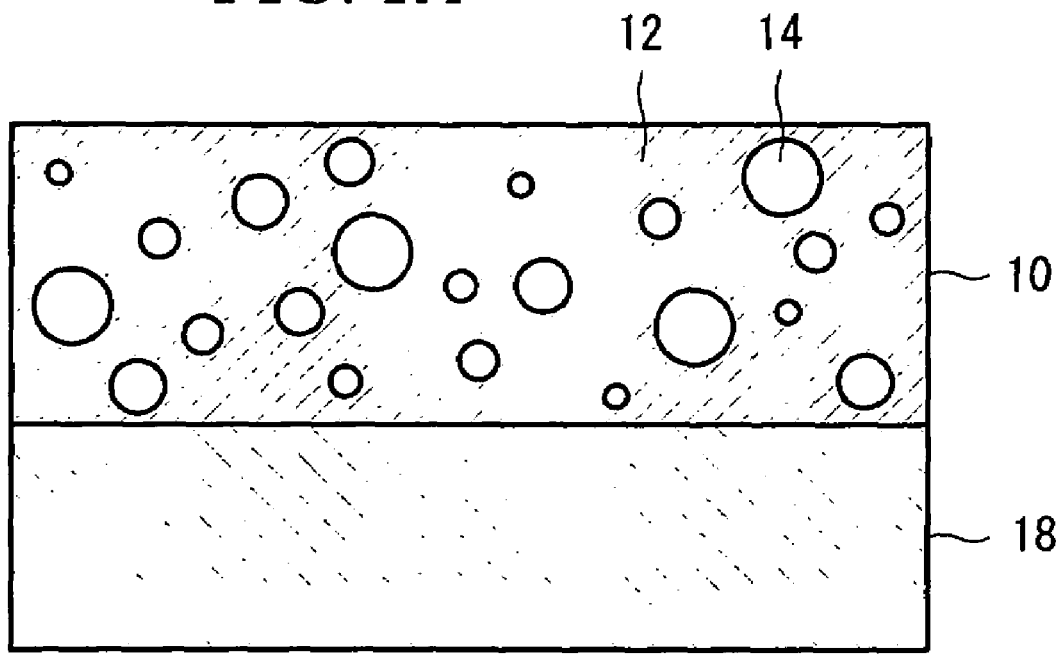
FIGS. 1A and 1B are sectional views of samples.
Figure 1B:
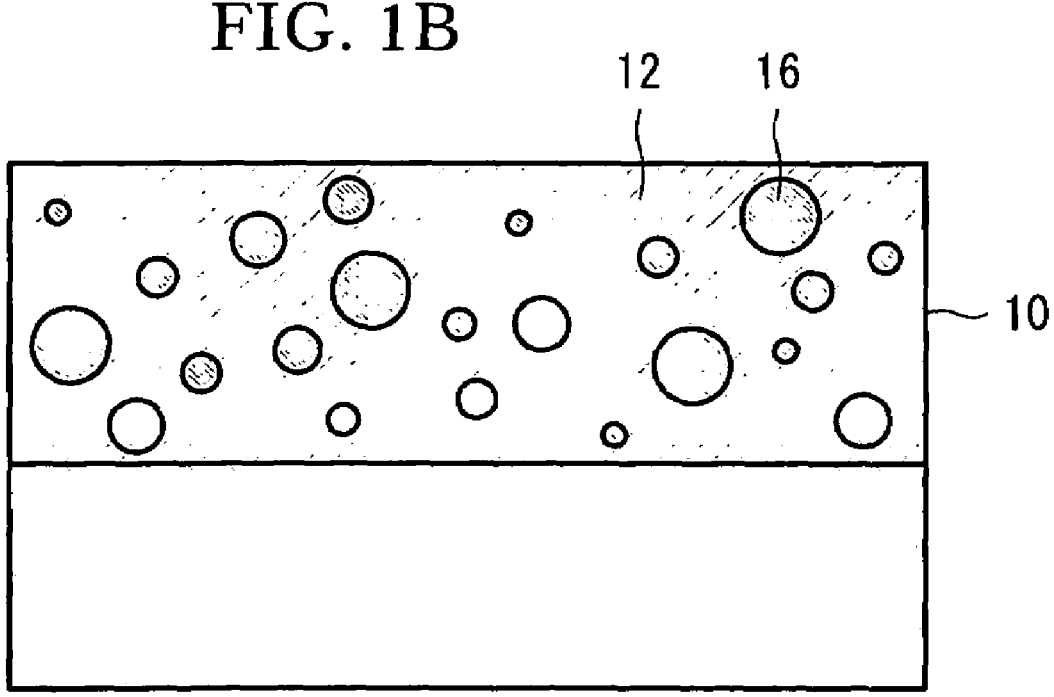

Embodiments of the present invention will now be described below with reference to the drawings. Before entering the explanation of the embodiments of the present invention, a method for calculating a void content will be described in the case of a thin film having a known matrix density. When a thin film having no voids and another thin film having voids can be prepared and the matrices of these thin films are the same material, i.e., the same matrix density, the void content of the thin film having voids can be calculated as described below. First, the density of the thin film having no voids is measured by the X-ray reflectance method, the result being a matrix density $\rho_M$. Next, the density of the thin film having voids is measured by the X-ray reflectance method, the result being an average density $\rho_F$ of the thin film having voids. Expressing a void density as $\rho_{pore}$ and a void content as p, formula (1) in FIG. 2 is effected. Since the void density $\rho_{pore}$ is zero, the void content p becomes formula (2) in FIG. 2. Then, if the matrix density $\rho_M$ is determined by the X-ray reflectance method, the void content can be calculated with a high accuracy.

When particles are dispersed in the matrix in place of the voids, it is needed only to exchange the void density $\rho_{pore}$ to a particle density $\rho_{par}$ in formula (1), the result being shown as formula (34) in FIG. 20. In this case, if the particle density $\rho_{par}$ is known, the particle content p can be calculated with the use of the average density $\rho_F$ of the thin film having particles, which can be measured by the X-ray reflectance method, and the density $\rho_M$ of the thin film having no particles, which can be also measured by the X-ray reflectance method if such a thin film is prepared.

Although the above-described method for calculating the void content or the particle content when the matrix density is known is not included in the present invention, such an explanation would become the basic knowledge for understanding the present invention.

The first aspect of the present invention will now be described. The point of the first aspect is that when a thin film having a known void content or particle content can be prepared, an equipment constant of an X-ray small angle scattering measurement equipment can be determined using such a thin film and then a void content or particle content of a thin film having an unknown void content or particle content can be determined based on the equipment constant. Thinking about a thin film having voids, there occurs a scattered X-ray caused by the difference in density of electrons between the matrix and the void, the scattered X-ray intensity I being expressed by formula (3) in FIG. 2, where $k_0$ is the equipment constant, p is the void content, $r_e$ is the radius of a classical electron orbit, $f_F$ is an average atomic scattering factor of the thin film, $M_f$ is an average atomic mass of the thin film, $\rho_F$ is an average density of the thin film, and F is a scattering function. The scattering function F is a function of a scattering vector q and a parameter "para". The scattering vector q depends on an X-ray incident angle against the thin film, an X-ray outgoing angle from the thin film and an X-ray wavelength used. The parameter "para" depends on a scattering function model. The form of the scattering function f will be described later. The equipment constant $k_0$ is a coefficient depending on the brightness of the incident X-ray, a geometric arrangement of the equipment, a slit size and so on, it being a specific value inherent in the equipment.

In formula (3) in FIG. 2, the scattered X-ray intensity I on the left side is a value actually detected with an X-ray detector, whereas a part between two absolute-value symbols on the right side can be calculated using a theoretical formula. Stating in detail, the average atomic scattering factor $f_F$, the average atomic mass $M_f$ and the average density $\rho_F$ may be numerical values. The scattering function F may be calculated with variable parameters. The average density $\rho_F$ may be a value measured by the X-ray reflectance method, or may be a predetermined value if it is known by any other method. Accordingly, an unknown term in formula (3) is $k_0 p/(1-p)$ only, which is that determined as a result of the profile fitting operation as described below, it being expressed by S and being called as a scale factor. Then, formula (3) in FIG. 2 becomes formula (4), and the scale factor S in formula (4) is expressed by formula (5). Formula (5) is the basic formula indicating a relationship among the scale factor S, the equipment constant $k_0$ and the void content p. Transforming formula (5) so that the equipment constant $k_0$ moves on the left side, formula (6) is effected. When the scale factor S is determined by the X-ray small angle scattering method for a thin film having a known void content p, the right side of formula (6) can be calculated and the equipment constant $k_0$ can be determined. When the equipment constant $k_0$ is determined, the void content p can be calculated, as seen from formula (7), using the scale factor S and the equipment constant $k_0$ after the scale factor S was determined by the X-ray small angle scattering method for a thin film having an unknown void content p. The description above is the principle of calculation of the void content according to the first aspect of the present invention.

Incidentally, formula (4) mentioned above should be, strictly speaking, expressed by formulae (37) to (41) in FIG. 22. Namely, the scattered intensity I is a sum of four scattered intensities $I_a$ to $I_d$. The intensity $I_a$ is one caused by a phenomenon in which an incident X-ray is scattered by the voids or particles in the thin film. The intensity $I_b$ is one caused by a phenomenon in which the incident X-ray which has been scattered by the voids or particles is further reflected at the boundary. The intensity $I_c$ is one caused by a phenomenon in which the incident X-ray which has been reflected at the boundary is further reflected at the voids or particles. The intensity $I_d$ is one caused by a phenomenon in which the incident X-ray which has been reflected at the boundary and further reflected at the voids or particles is further reflected at the boundary, i.e., multiple reflections. The total intensity I becomes a scattered intensity I in the thin film having voids or particles. Explaining symbols appearing in formulae (38) to (41), $q_L^+$ is a scattering vector and is expressed by formula (42) in FIG. 23. The symbol $q_L^-$ is also a scattering vector and is expressed by formula (43). The symbol $v_0$ is a wavenumber vector and is expressed by formula (44). The symbol $\alpha_L$ is a refraction angle at the incidence and is expressed by formula (45). The symbol $\zeta_L$ is a refraction angle at the outgoing and is expressed by formula (46). The symbol Im represents the imaginary part of a complex number. The symbol $d_L$ is the thickness of a thin film, the film thickness value determined by the X-ray reflectance method being substituted for $d_L$. The suffix L represents the Lth layer. Stating in detail, when the thin film is made of a multilayer, the scattered intensity is determined for each layer, L=1, 2, 3, . . . , and the L intensities are summed up. It is noted that although the scattering function F is a function of the parameter "para", it is omitted in expression in formulae (38) to (41).

Referring to formulae (42) and (43) in FIG. 23, the symbol Re represents real part of a complex number. The symbol λ in formula (44) is the wavelength of the incident X-ray. The symbol $\theta_0$ in formula (45) is an incident angle of an X-ray which is incident on the thin film. The symbol $n_L$ is a refraction index of the thin film, which can be easily calculated from the average density of the thin film. The average density may be an average density $\rho_F$ determined by the X-ray reflectance measurement. The symbol $\phi_0$ in formula (46) is an outgoing angle of an X-ray which outgoes from the thin film.

The determination of the scattered intensity for the thin film having voids or particles as shown in formulae (37) to (46) is known and disclosed in the second publication mentioned above, for example.

A method for determining a particle content according to the first aspect will now be described. Thinking about a thin film having particles, there occurs a scattered X-ray caused by the difference in density of electrons between the matrix and the particle, the scattered X-ray intensity I being expressed by formula (8) in FIG. 3, where $f_{par}$ is an average atomic scattering factor of the particle, $M_{par}$ is an average atomic mass of the particle, $\rho_{par}$ is an average density of the particle, and other symbols are the same as in formula (3). Formula (8) can be transformed to formula (9) using the scale factor S. If the particle density $\rho_{par}$ is known, the scale factor S can be determined by the profile fitting operation in the X-ray small angle scattering method similarly to the case having the voids. The scale factor S has the same form as formula (5) mentioned above. Accordingly, when the scale factor S is determined by the X-ray small angle scattering method for the thin film having a known particle content p, the equipment constant $k_0$ can be determined. When the equipment constant $k_0$ is determined, the particle content p can be calculated using the scale factor S and the equipment constant $k_0$ after the scale factor S was determined by the X-ray small angle scattering method for a thin film having an unknown particle content p. The description above is the principle of calculation of the particle content according to the first aspect of the present invention.

It is noted that formula (8) is based on that the particle density $\rho_{par}$ is known, formula (8) is not applicable to the case that the particle density is unknown. However, if the matrix density $\rho_M$ is known in such a case, a scattered X-ray intensity can be determined using formula (28) in FIG. 20. Formula (28) can be transformed to formula (29) using the scale factor S. Thus, if the matrix density $\rho_M$ is known, the scale factor S can be determined by the profile fitting operation in the X-ray small angle scattering method similarly to the case having voids, the scale factor S having the form of formula (30). Accordingly, when the scale factor S is determined by the X-ray small angle scattering method for the thin film having a known particle content p, the equipment constant $k_0$ can be determined. When the equipment constant $k_0$ is determined, the particle content p can be calculated, as seen from formula (32), using the scale factor S and the equipment constant $k_0$ after the scale factor S was determined by the X-ray small angle scattering method for a thin film having an unknown particle content p. The description above is another method of calculation of the particle content according to the first aspect of the present invention.

The second aspect of the present invention will now be described. The second aspect is used in the case that a thin film having no voids is not available. In this case, there are prepared a plurality of samples which have matrix densities expected to be identical with each other whereas void contents expected to be different from each other. Generally speaking, a void content $p_i$ of the ith sample is expressed by formula (10) in FIG. 3, $\rho_{Fi}$ being an average density of the ith sample and $\rho_{Mi}$ being a matrix density of the ith sample. The scattered X-ray intensity I(i) caused by the difference in density of electrons between the matrix and the void can be expressed by formula (11) in FIG. 3, this formula having the same form as formula (3) except the difference of having the symbol indicating the ith number. Formula (11) can be transformed to formula (12) using the scale factor $S_i$ which is be expressed by formula (13).

Since the equipment constant $k_0$ does not depend on the sample, a relational expression shown in (14) is effected based on formula (13). Namely, there is effected a relational expression between the scale factor S and the void content p among plural samples. Since the void content p can be expressed using the average density $\rho_F$ and the matrix density $\rho_M$ of the sample as shown in formula (2) in FIG. 2, formula (2) is applied to formula (14) to effect formula (15). Further, formula (16) is effected based on formula (14), and formula (17) is effected based on formula (15).

Referring to formula (16), the void content $p_1$ of a sample 1 is expressed by the scale factor $S_1$ of the sample 1, the scale factor $S_0$ of a sample 0 and the void content $p_0$ of the sample 0. The void factor of the sample 2 or a sample having a larger number is expressed by the scale factor of the sample in question, the scale factor $S_0$ of a sample 0 and the void content $p_0$ of the sample 1. After all, the void content of each sample is expressed by the void content $p_0$ of only one sample, e.g., sample 0, through the mediation of the scale factor S. This means that if the scale factors S of the samples have been determined and the void content $p_0$ of one sample is determined, the void contents of other samples can be easily calculated.

Referring to formula (17), the matrix density $\rho_{M1}$ of a sample 1 is expressed by the scale factor $S_1$ of the sample 1, the average density $\rho_{F1}$ of the sample 1, the scale factor $S_0$ of the sample 0, the average density $\rho_{F0}$ of the sample 0, and the matrix density $\rho_{M0}$ of a sample 0. The matrix density of the sample 2 or a sample having a larger number is similarly expressed. Namely, the matrix density of each sample is expressed by the matrix density $\rho_{M0}$ of only any one sample, e.g., sample 0, through the mediation of the scale factor S and the average density $\rho_F$. This means that if the scale factors S and the average densities $\rho_F$ of the samples are determined and the matrix density $\rho_{M0}$ of any one sample is determined, the matrix densities of other samples can be easily calculated.

In formula (17), unknown items are matrix densities $\rho_{M0}$, $\rho_{M1}$, $\rho_{M2}$, $\rho_{M3}$, . . . and the number of the unknown items is equal to the number of the samples, while the number of the formulas in question is less than the number of the samples by one. Therefore, the provisions are insufficient to solve formula (17). Then, it is assumed that the matrix densities of the plural samples are identical with each other. In other words, such samples should be the objects to be measured. In this case, formula (17) can be solved by adding the provision of "the difference in matrix density among the samples becomes a minimum". Such a provision can be expressed by formula (18) in FIG. 5. The left side of the formula (18) represents what should be a minimum in connection with the matrix densities $\rho_{M0}$, $\rho_{M1}$, $\rho_{M2}$, . . . and uses the function name of "MinFun". The right side shows the form of the function, the numerator being a square root of the sum, for all of the combinations of two samples, of the square of the difference between the matrix density $\rho_{Mi}$ of the ith sample and the matrix density $\rho_{Mj}$ of the jth sample, while the denominator being the sum of the matrix densities of all of the samples. It is noted that each of the matrix densities of the samples becomes a function of the matrix density $\rho_{M0}$ of one sample as shown in formula (17) and thus formula (18) becomes a function of the matrix density $\rho_{M0}$ only. Then, when differentiating formula (18) with the matrix density $\rho_{M0}$ and allowing the resultant to be zero as shown in formula (19), this operation would satisfy the provision that the difference in matrix density among the samples becomes a minimum. When the formula (19) is solved, the matrix density $\rho_{M0}$ of the sample 0 is determined. When the matrix density $\rho_{M0}$ is determined, the matrix densities $\rho_{M1}$, $\rho_{M2}$, $\rho_{M3}$, . . . of the other samples can be calculated based on formula (17). When the matrix density $\rho_M$ of each sample is determined, the void content p can be calculated based on formula (2). The description above is the principle of calculation of the void content according to the second aspect of the present invention.

Furthermore, when the void content is calculated, the equipment constant $k_0$ can be determined using formula (6) in FIG. 2. When the equipment constant $k_0$ is determined, thereafter, as in the first aspect, the void content can be calculated based on formula (7) in FIG. 2 even for the sample having a different matrix density as long as the scale factor S is determined.

Explaining an example of calculation of formula (19), the case using three samples will be described below. The matrix density $\rho_{M0}$ of the sample 0 becomes formula (20) in FIG. 6. Namely, the matrix density $\rho_{M0}$ of the sample 0 can be calculated with the use of the scale factors $S_0$, $S_1$ and $S_2$ and the average densities $\rho_{F0}$, $\rho_{F1}$ and $\rho_{F2}$ of the samples 0, 1 and 2. Each of the average densities of the samples can be measured by the X-ray reflectance method, and each of the scale factors can be determined by the X-ray small angle scattering method. When the matrix density $\rho_{M0}$ is determined, the matrix densities $\rho_{M1}$ and $\rho_{M2}$ can be calculated using formulae (21) and (22), thus the matrix densities of the three samples can be determined.

A method for determining a particle content according to the second aspect will now be described. A theoretical profile of the scattered intensity is produced, for plural samples, with the use of formula (9) in FIG. 3 including the particle density $\rho_{par}$, and a fitting operation is carried out between the measured profile of the scattered intensity and the theoretical profile to determine the scale factor S. On the other hand, the matrix density of each sample can be expressed by formula (23) in FIG. 6, which corresponds to formula (17) for the voids. The matrix density $\rho_{M1}$ of the sample 1 is expressed by the scale factor $S_1$ of the sample 1, the average density $\rho_F$ of the sample 1, the particle density $\rho_{par1}$ of the sample 1, the scale factor $S_0$ of the sample 0, the average density $\rho_F$ of the sample 0, the particle density $\rho_{par0}$ of the sample 0 and the matrix density $\rho_{M0}$ of the sample 0. The matrix density of the sample 2 or a sample having a larger number is expressed similarly. After all, the matrix density of each sample is expressed by the matrix density $\rho_{M0}$ of only one sample, e.g., sample 0, through the mediation of the scale factor S, the average density $\rho_F$ and the particle density $\rho_{par}$. This means that if the scale factors S, the average density $\rho_F$ and the particle density $\rho_{par}$ of the samples have been determined and the matrix density $\rho_{M0}$ of one sample is determined, the matrix densities of other samples can be easily calculated.

As in the case having the voids, the matrix density $\rho_{M0}$ can be calculated by solving formula (19) in FIG. 5. When the matrix density $\rho_{M0}$ is determined, the matrix densities $\rho_{M1}$, $\rho_{M2}$, $\rho_{M3}$, ... of the other samples can be calculated based on formula (23). When the matrix density $\rho_M$ of each sample is determined, the particle content p can be calculated based on formula (24) in FIG. 6, which is the transformation of formula (34) in FIG. 20. The description above is the principle of calculation of the particle content according to the second aspect of the present invention.

In the second aspect described above, when there is no thin film having a known void content or particle content, the equipment constant is determined in a manner that there are prepared a plurality of samples having void or particle contents which are different from each other under the provision that "the particle density is known", and the matrix densities are determined so that the matrix densities are identical with each other to determine the equipment constant. On the contrary, it may be contemplated that the particle density is unknown while "the matrix density is known". In such a case, the third aspect should be used as described below.

In the third aspect, a theoretical profile of the scattered intensity is produced, for plural samples, with the use of formula (28) in FIG. 20 including the matrix density $\rho_M$, and a fitting operation is carried out between the measured profile of the scattered intensity and the theoretical profile to determine the scale factor S. In this case, formulae (33) and (35) are effected, and the particle density of each sample is expressed by formula (36) in FIG. 21, which corresponds to formula (23) for the second aspect. The particle density $\rho_{par0}$ can be determined so that the difference in particle density becomes a minimum by solving the minimum provision, for the particle density $\rho_{par}$, similar to formula (19) in FIG. 5. When the particle density $\rho_{par0}$ is determined, the particle densities $\rho_{par1}$, $\rho_{par1}$, ... of the other samples can be calculated based on formula (36). Further, when the particle density $\rho_{par}$ of each sample is determined, the particle content can be calculated based on formula (24). The description above is the principle of calculation of the particle content according to the third aspect of the present invention.

The scattering function F in formula (3) will now be described. The scattering function may be one of some functions, typically the functions shown by formulae (25) and (26) in FIG. 18. Formula (25) shows a model which uses the average diameter $D_0$ of the void or particle and the variance $\sigma$ indicating the distribution of the diameter, where $Q(D,D_0,\sigma)$ is a diameter distribution function of the void or particle, the D being a variable representing the diameter. On the other hand, formula (26) shows a Debye model which uses the correlation distance $\xi$ of the electron density fluctuation. The selection of the models depends on the state of the voids or particles in the sample. Formula (25) is a model function effective in a system in which the void or particle has a specific shape, a sphere for example. On the contrary, formula (26) is known as a model function, a type of two-layer separation, effective in a system in which the voids or particles are confusing like an ant nest. The embodiment described below uses the model function of formula (25) to determine the theoretical profile of the scattered intensity.

The average atomic scattering factor $f_F$ and the average atomic mass $M_F$ appearing in formula (3) will now be described. The atomic scattering factor f can be calculated by formula (27) in FIG. 19 and is expressed by a factor $f_0$ which does not depend on the wavelength and abnormal dispersions $f_1$ and $f_2$ which depend on the wavelength. The symbol i in the formula represents an imaginary number. The factor $f_0$ depends on the scattering angle and is substantially equal to the atomic number Z in the small angle scattering region. The embodiment described below uses, as a sample, MSQ (methyl silsesquioxane, chemical formula being $Si_2O_3C_2H_6$). The average atomic scattering factor $f_F$ and the average atomic mass MF of the MSQ are shown in a Table in FIG. 19, the X-ray wavelength being assumed to be CuKα, 0.154178 nm.

Figure 7A:
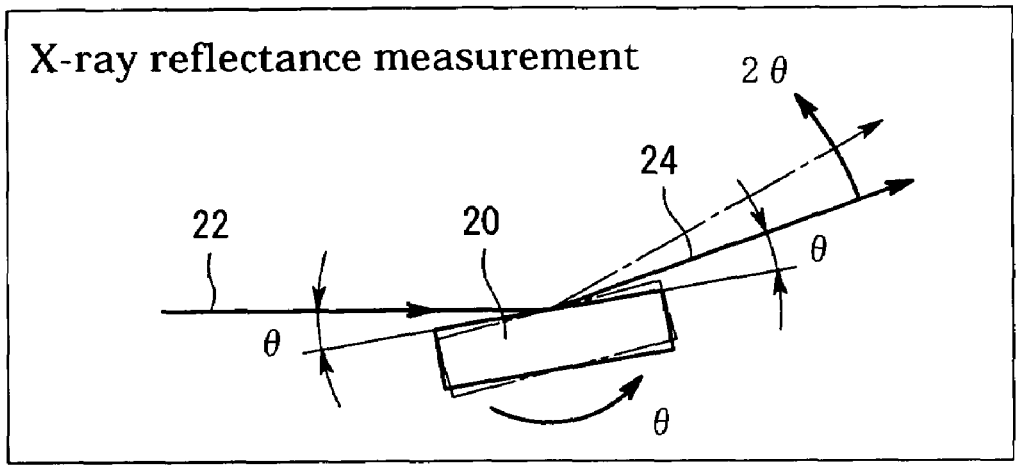
FIGS. 7A to 7C are explanatory views of X-ray reflectance measurement and X-ray small angle scattering measurement.

Actual measurement examples will now be described. Examples of void content measurement according to the second aspect of the present invention will be shown for three porous MSQ thin films which are expected to have different void contents. The three samples are expected to have the same but unknown matrix density. First, an X-ray reflectance profile was measured for each of the three samples, called as samples 0, 1 and 2, the method of the measurement being described briefly. FIG. 7A shows the X-ray reflectance measurement. An X-ray 22 is incident on the surface of a sample 20 at a minute incident angle θ. A reflected X-ray 24 is detected in a direction of an outgoing angle θ, the same as the incident angle, from the surface of the sample 20. Assuming that the position of the incident X-ray 22 is stationary, the sample is rotated with a θ-rotation and the X-ray detector, i.e., the direction of the reflected X-ray 24, is rotated with a 2θ-rotation, so that a variation of an X-ray reflectance, i.e., a ratio of a reflected X-ray intensity to an incident X-ray intensity, is recorded to obtain an X-ray reflectance profile.

Figure 8:
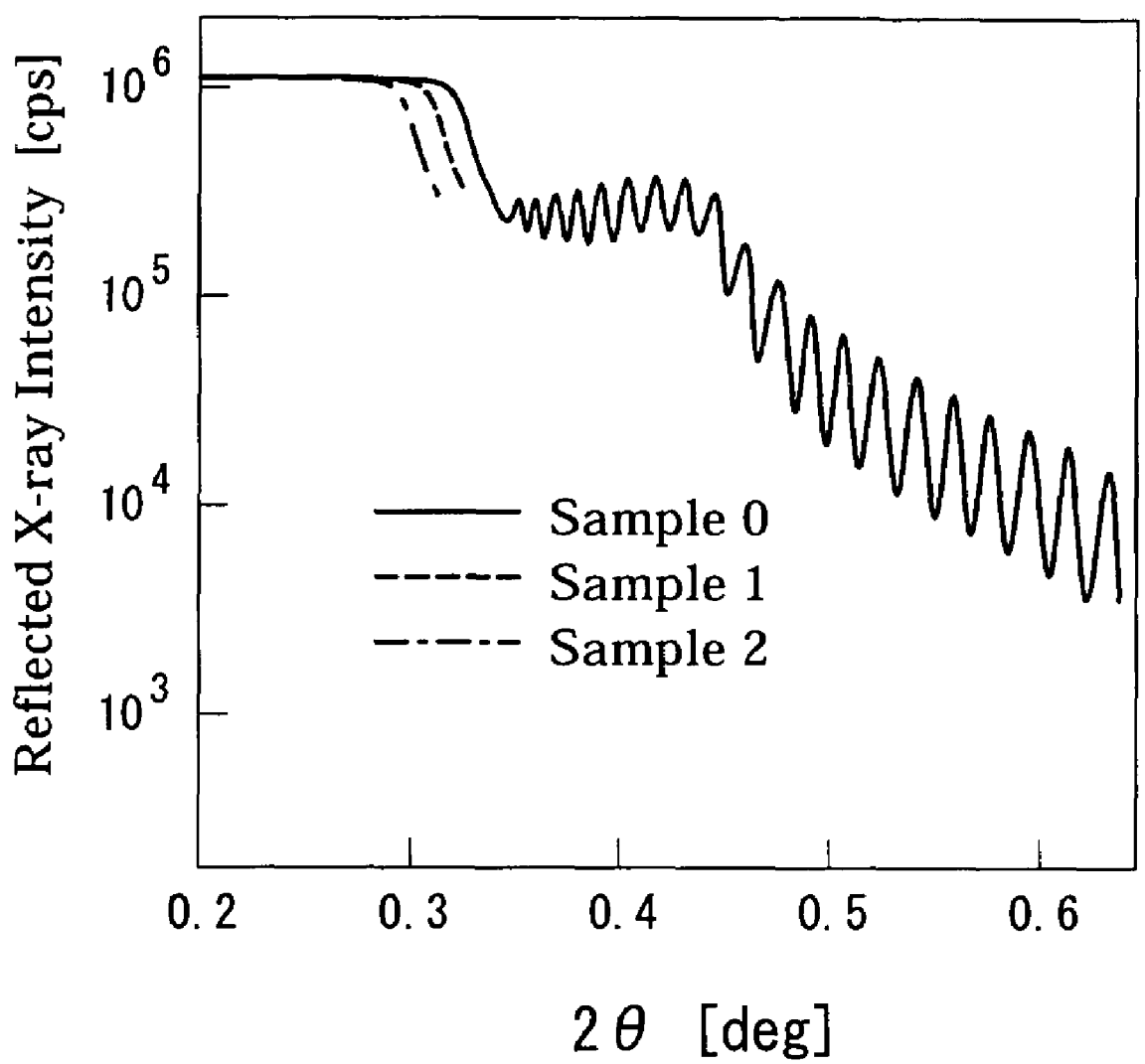
FIG. 8 is a graph showing results of the X-ray reflectance measurement.

FIG. 8 is a graph showing the measurement result of the X-ray reflectance profiles for the three samples, 2θ in abscissa and a reflected X-ray intensity in ordinate. A solid line represents a profile of the sample 0, a broken line represents a profile of the sample 1 and a chain line represents a profile of the sample 2, noting however that the profiles for the samples 1 and 2 shown are limited, for avoiding complication, to only the starting regions in which the reflectance begins to decrease. It would be readily expected with the graph that the void contents of the samples are different from each other because the critical angles of the total reflection, i.e., the angle at which the reflectance begins to decrease, of the three samples are different from each other. A parameter fitting operation is carried out between the measured X-ray reflectance profile and the theoretical X-ray reflectance profile to determine the film thickness and the density of the sample and the roughness of the boundary between the thin film and the substrate, the parameter fitting operation being known, as disclosed in the third publication mentioned above, and detailed explanation thereof being omitted. FIG. 9 shows a table indicating parameters determined by the fitting operation. Now, the average density and the roughness have been determined for the three samples. It is seen at least that the void contents of the three samples would be different from each other because of the same matrix material and the different average densities.

Figure 10:
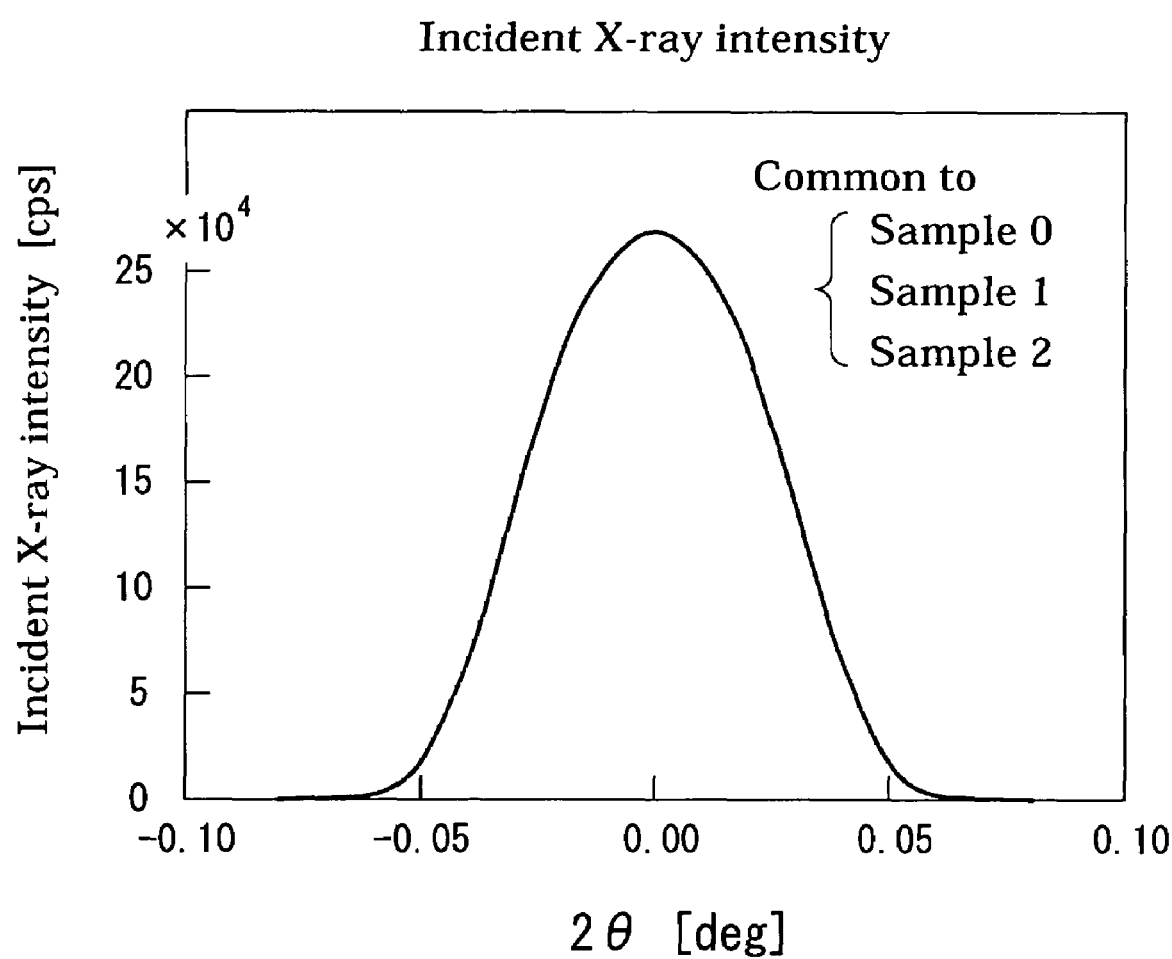
FIG. 10 is a graph showing an incident X-ray intensity.

Next, an X-ray small angle scattering measurement was carried out for each of the three samples. An incident X-ray intensity profile was measured for each sample for confirmation on the occasion of the X-ray small angle scattering measurement for the three samples, the result being shown in FIG. 10. The graph in FIG. 10 shows three incident X-ray intensity profiles superimposed on each other, but shows one curve because these profiles are perfectly superimposed. It is understood with the graph that incident X-ray intensities are identical with each other in the X-ray small angle scattering measurement for the three samples. The X-ray small angle scattering profiles were measured under these conditions.

Figure 7B:
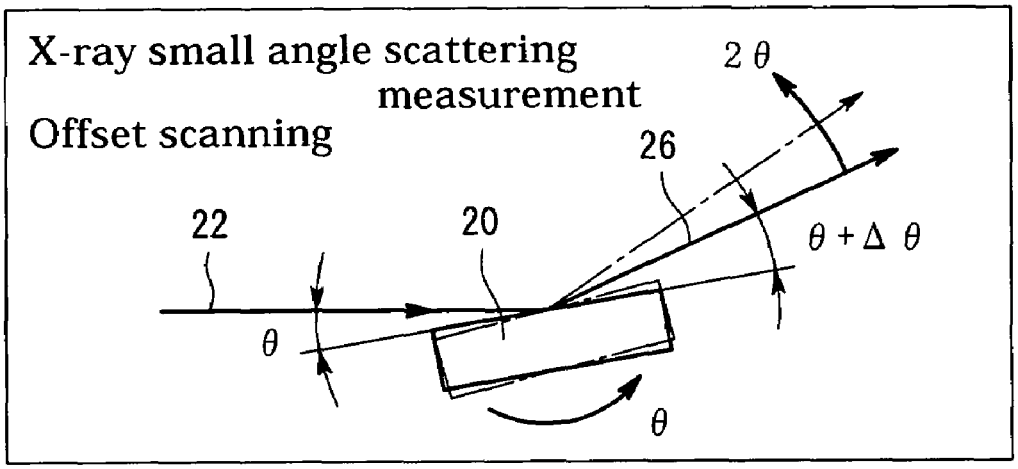

There will now be explained an offset scanning profile and a rocking scanning profile in the X-ray small angle scattering method. FIG. 7B shows a method for measuring the offset scanning profile. An X-ray 22 is incident on the surface of a sample 20 at a minute incident angle θ. A scattered X-ray 26 is detected in a direction of an outgoing angle "θ+Δθ" from the surface of the sample 20. Namely, the outgoing angle is offset by Δθ compared to the incident angle. The offset allows the intense total-reflected X-ray not to enter the X-ray detector. Assuming that the position of the incident X-ray 22 is stationary, the sample is rotated with a θ-rotation and the X-ray detector, i.e., the direction of the scattered X-ray 26, is rotated with a 2θ-rotation, so that a variation of the scattered X-ray intensity is recorded to obtain an offset scanning profile. In general, the profile is measured in a range between 0 to 8 degrees in 2θ.

Figure 7C:
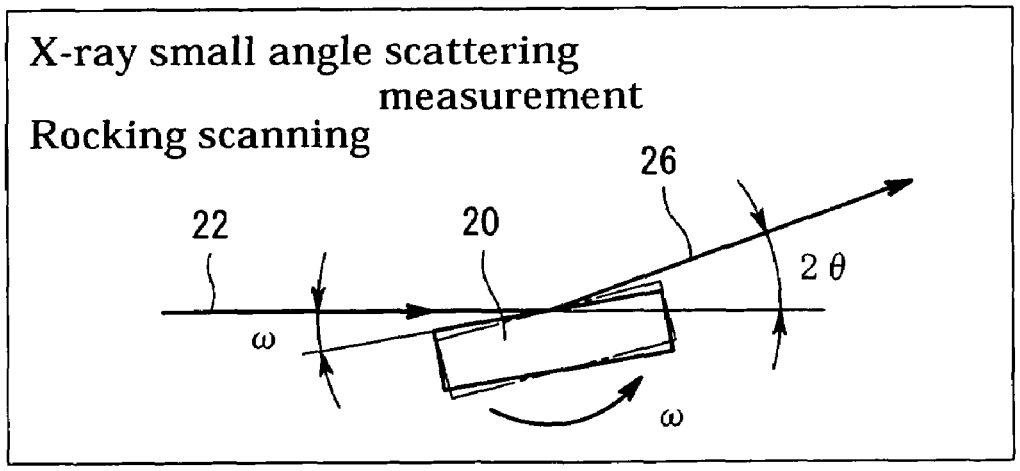

FIG. 7C shows a method for measuring the rocking scanning profile. An X-ray 22 is incident on the surface of a sample 20 at a minute incident angle ω. A scattered X-ray 26 is detected in a direction which is at 2θ against the incident X-ray 22 and is set stationary. Assuming that the position of the incident X-ray 22 is stationary, only the sample is rotated with an ω-rotation, so that a variation of the scattered X-ray intensity is recorded to obtain a rocking scanning profile.

Figure 11:
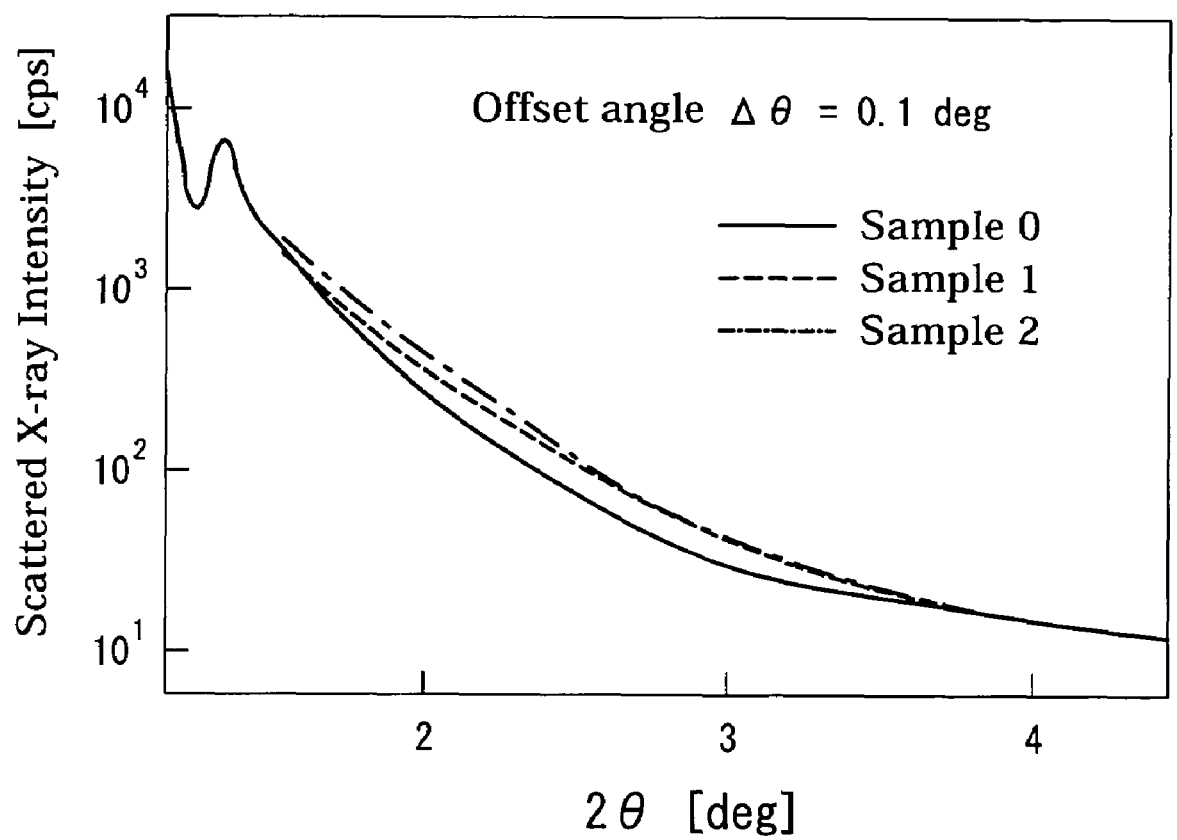
FIG. 11 is a graph showing results of the offset scanning in the X-ray small angle scattering measurement.

FIG. 11 is a graph showing the offset scanning profiles of the X-ray small angle scattering for the three samples. The offset angle Δθ is 0.1 degree. A profile fitting, i.e., the parameter fitting, operation is carried out, for the three measured profiles, between the measured profile and the theoretical profile.

Figure 12:
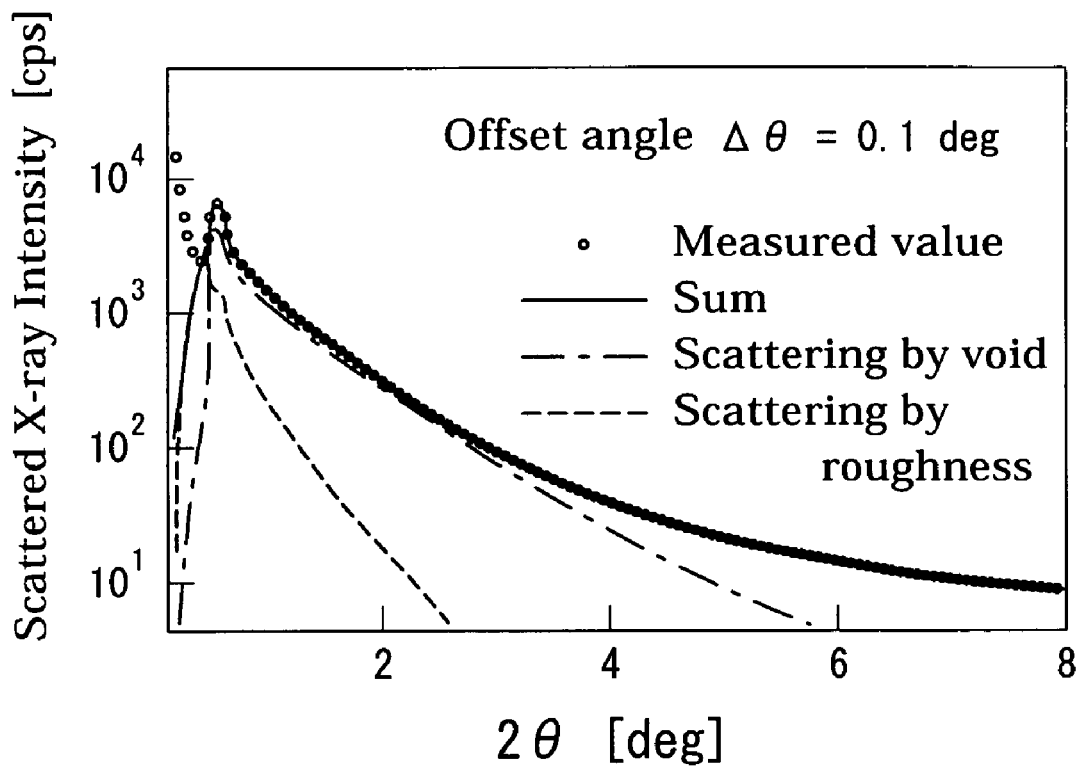
FIG. 12 is a graph showing profile fitting for the offset scanning in the X-ray small angle scattering measurement.

FIG. 12 is a graph showing the profile fitting on the offset scanning profile of the X-ray small angle scanning for the sample 1. The offset angle Δθ is 0.1 degree. Small circles indicate the measured value and the assembly thereof becomes the measure profile. The chain line represents the theoretical profile of the scattered X-ray intensity caused by the voids, the intensity being determined using formulae (37) to (41). The broken line represents the theoretical profile of the scattered X-ray intensity caused by the roughness of the surface boundary, the intensity being calculated using known theoretical formula as disclosed in the second publication mentioned above. The solid line represents the sum of the two theoretical profiles. The parameters are changed so that the total theoretical profile approaches the measured profile as close as possible to select the optimum parameters. If the scattered intensity caused by the voids is far larger than the scattered intensity caused by the roughness, the scattered intensity caused by the roughness may be omitted in the fitting operation. The embodiment uses, as the scattering function, a model function of formula (25) mentioned above, in which spherical voids are randomly dispersed in the thin film and the distribution of the void size conforms to the Gamma distribution function.

Figure 13:
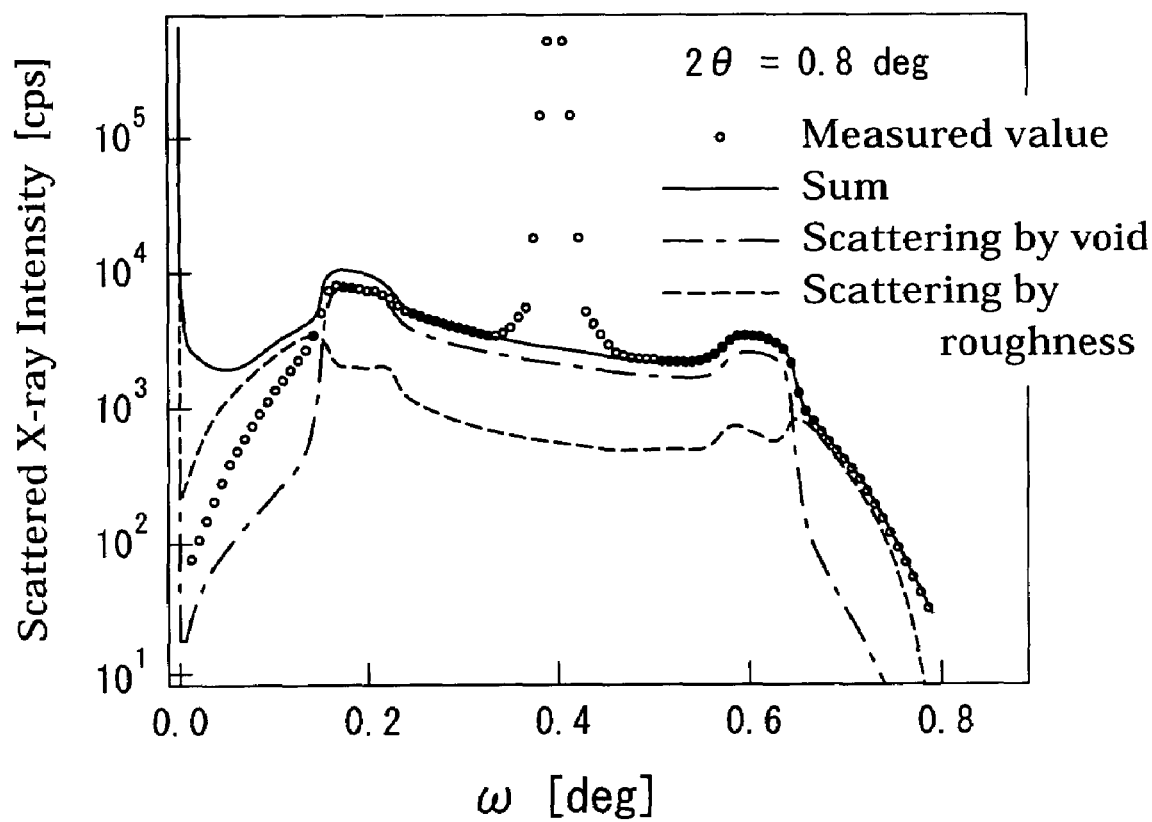
FIG. 13 is a graph showing profile fitting for the rocking scanning in the X-ray small angle scattering measurement.

FIG. 13 is a graph showing the profile fitting on the rocking scanning profile of the X-ray small angle scanning for the sample 1, the angle 2θ being 0.8 degree. It should be noted that the large measured peak at the center of the graph is caused the total reflection and thus not the scattered X-ray caused by the voids. The total reflection peak should be ignored in the profile fitting operation with the theoretical profile.

In the actual measurements, the offset scanning profile fitting operation as shown in FIG. 12 was carried out for each of the three samples and then the rocking scanning profile fitting operation as shown in FIG. 13 was carried out for each of the three samples. The rocking scan profile fitting operations were carried out with 0.6, 0.8, 1.0, 1.2 and 1.5 degrees in 2θ. The profile fitting operations should be carried out ideally at the same time between the measured values and the theoretical values for all of the offset scanning profiles and the rocking scanning profiles in a manner that the parameters are determined so that the difference becomes a minimum. The method of nonlinear least squares is effectively used for the minimization of the difference.

As a result of the fitting mentioned above, the average diameter of the void and the variance indicating the diameter distribution, the variance of the Gamma distribution function, were determined as the parameters as shown in FIG. 14 and further the scale factor S was determined from the X-ray intensity on that occasion.

A method for calculating the matrix density from the scale factor S and the average density $\rho_F$ will now be described. The average density $\rho_F$ has been determined and is shown in FIG. 9. The scale factor S has been determined in the X-ray small angle scattering method and is shown in FIG. 14. Then, these values are substituted into formula (20) in FIG.

5 to calculate the matrix density $\rho_{M0}$ of the sample 0, the resultant value being 1.412. Further, the matrix densities $\rho_{M1}$ and $\rho_{M2}$ of the sample 1 and sample 2 are calculated using formulae (21) and (22) in FIG. 6, the resultant values being 1.413 and 1.412. The void content p is calculated using the matrix densities in formula (2) in FIG. 2, the void contents of the three samples being $p_0$=0.175, $p_1$=0.237 and $p_2$=0.296 respectively. These results are shown in the table in FIG. 17.

Figure 15:
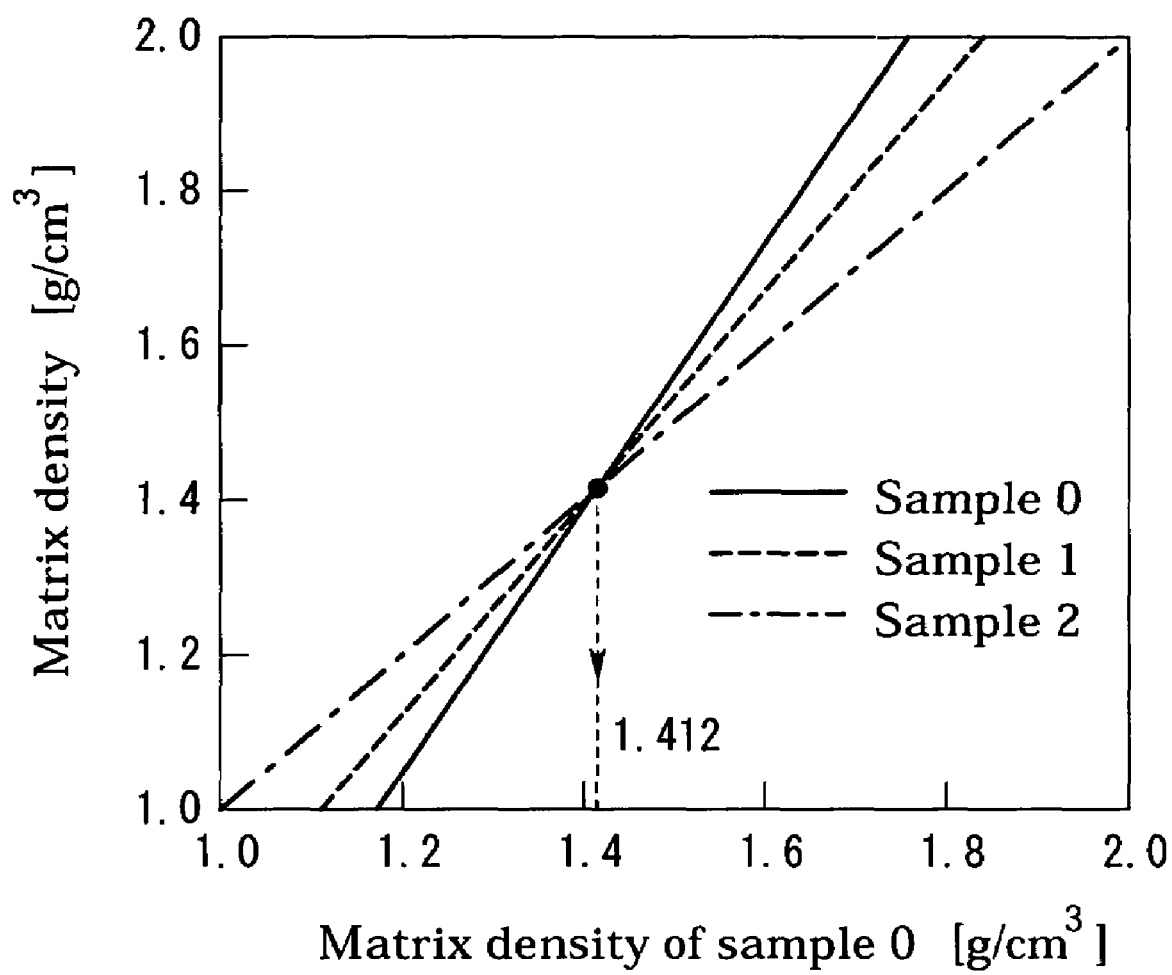
FIG. 15 is a graph showing relative matrix densities among the samples.

The minimization of the difference in matrix densities among the samples will now be described from another viewpoint. FIG. 15 is a graph showing relationships of formula (17) in connection with the matrix densities of the three samples, the matrix density $\rho_{M0}$ of the sample 0 in abscissa and the matrix densities $\rho_{M0}$, $\rho_{M1}$ and $\rho_{M2}$ of the three samples in ordinate. The average densities $\rho_{F0}$, $\rho_{F1}$ and $\rho_{F2}$ and the scale factors $S_0$, $S_{1\ and\ S2}$ in formula (17) receive the values shown in the table in FIG. 17. Thinking about the sample 0 and the sample 1, the matrix densities of the samples become identical with each other at the intersection of the two straight lines. The matrix density at the intersection is the value which allows the difference in the two matrix densities to be a minimum, i.e., zero. Accordingly, if at least two samples are measured, the matrix density can be determined.

Furthermore, thinking about the three samples, three intersections exist among the three straight lines. It is noted however that the graph shown in FIG. 15 the three straight lines are intersected with each other at almost the same point, the matrix density at the intersection being 1.412. The fact that three intersections are at almost the same point represents a high reliability of the matrix density determined by the present invention. If the three intersections are apart from each other, the reliability of the matrix density calculated using formula (20) would be poor. Thus, it would be preferable to carry out the second aspect for at least three samples as shown in FIG. 15 for confirming the reliability of the matrix density.

Figure 16:
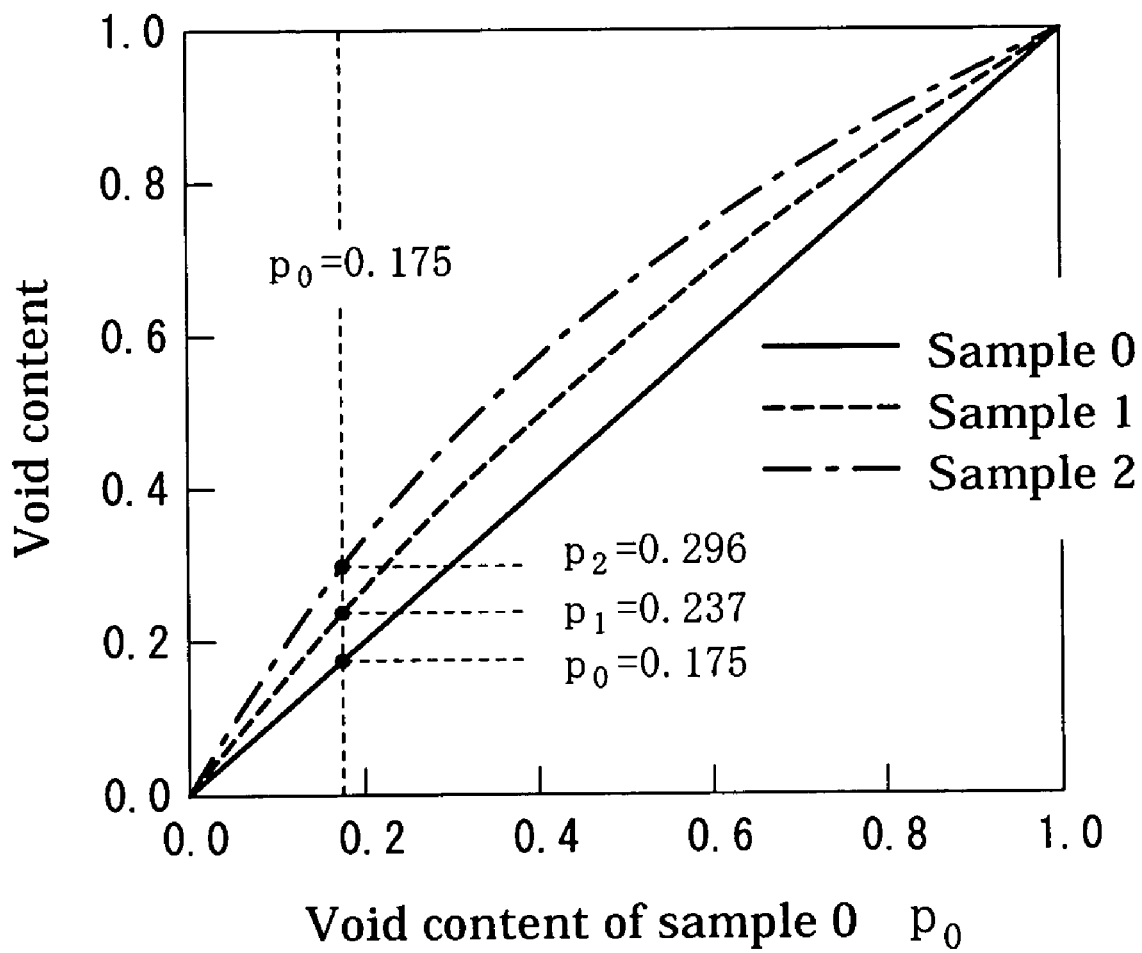
FIG. 16 is a graph showing relative void contents among the samples.

FIG. 16 is a graph showing the relationships of formula (16) in connection with the void densities of the three samples. It is understood that when the void content $p_0$ of the sample 0 is determined, the void contents of the sample 1 and the sample 2 are easily calculated.

Although the average density and the film thickness of the sample are determined by the X-ray reflectance method in the embodiments described above, these values may be acquired by another means, for example, they may be entered via a keyboard by an operator.

What is claimed is:

1. A method for measuring a void content of a sample which is made of a thin film having a matrix and voids dispersed in the matrix comprising the steps of:
   (a) preparing a first sample having a known void content and a second sample having an unknown void content;
   (b) executing an X-ray reflectance measurement for the first sample to get a first reflectance profile and determining an average density and a film thickness of the first sample based on the first reflectance profile;
   (c) executing an X-ray small angle scattering measurement for the first sample to get a first measured profile of a scattered X-ray intensity, and carrying out a parameter fitting operation between the first measured profile of the scattered X-ray intensity and a theoretical profile of the scattered X-ray intensity, which is calculated based on the average density and the film thickness of the first sample, to determine a first scale factor of the scattered X-ray intensity;
   (d) calculating an equipment constant of an X-ray small angle scattering measurement equipment based on the first scale factor and the known void content of the first sample;
   (e) executing an X-ray reflectance measurement for the second sample to get a second reflectance profile and determining an average density and a film thickness of the second sample based on the second reflectance profile;
   (f) executing an X-ray small angle scattering measurement for the second sample using the same X-ray small angle scattering measurement equipment as for the first sample to get a second measured profile of the scattered X-ray intensity, and carrying out a parameter fitting operation between the second measured profile of the scattered X-ray intensity and a theoretical profile of the scattered X-ray intensity, which is calculated based on the average density and the film thickness of the second sample, to determine a second scale factor of the scattered X-ray intensity;
   (g) calculating a void content of the second sample based on the equipment constant and the second scale factor; and
   (h) generating a signal indicative of the calculated void content.

2. An method for measuring a void content of a sample which is made of a thin film having a matrix and voids dispersed in the matrix, by performing steps of:
   (a) acquiring a film thickness of the sample;
   (b) acquiring an average density of the sample;
   (c) measuring a measured profile of a scattered X-ray intensity of the sample using X-ray small angle scattering measurement equipment;
   (d) producing a theoretical profile of the scattered X-ray intensity of the sample using the acquired film thickness and the acquired average density;
   (e) carrying out a parameter fitting operation between the measured profile of the scattered X-ray intensity measured by the X-ray small angle scattering measurement equipment and the theoretical profile of the scattered X-ray intensity, and calculating a scale factor of the scattered X-ray intensity;
   (f) acquiring a known void content of a first sample;
   (g) calculating an equipment constant of the X-ray small angle scattering measurement equipment based on the known void content of the first sample and a first scale factor calculated for the first sample;
   (h) calculating a void content of a second sample having an unknown void content based on a second scale factor calculated for the second sample and the calculated equipment constant; and
   (i) generating a singal indicative of the calculated void content.

3. A method for measuring a particle content of a sample which is made of a thin film having a matrix and particles, with a known particle density, dispersed in the matrix comprising the steps of:
   (a) preparing a first sample having a known particle content and a second sample having an unknown particle content;
   (b) executing an X-ray reflectance measurement for the first sample to get a first reflectance profile and determining an average density and a film thickness of the first sample based on the first reflectance profile;
   (c) executing an X-ray small angle scattering measurement for the first sample to get a first measured profile of a scattered X-ray intensity, and carrying out a parameter fitting operation between the first measured profile of the scattered X-ray intensity and a theoretical profile of the scattered X-ray intensity, which is calculated based on the average density, the film thickness and the particle density of the first sample, to determine a first scale factor of the scattered X-ray intensity;

(d) calculating an equipment constant of an X-ray small angle scattering measurement equipment based on the first scale factor and the known particle content of the first sample;

(e) executing an X-ray reflectance measurement for the second sample to get a second reflectance profile and determining an average density and a film thickness of the second sample based on the second reflectance profile;

(f) executing an X-ray small angle scattering measurement for the second sample using the same X-ray small angle scattering measurement equipment as for the first sample to get a second measured profile of the scattered X-ray intensity, and carrying out a parameter fitting operation between the second measured profile of the scattered X-ray intensity and a theoretical profile of the scattered X-ray intensity, which is calculated based on the average density, the film thickness and the particle density of the second sample, to determine a second scale factor of the scattered X-ray intensity;

(g) calculating a particle content of the second sample based on the equipment constant and the second scale factor; and (h) generating a signal indicative of the calculated particle content.

4. An method for measuring a particle content of a sample which is made of a thin film having a matrix and particles, with a known particle density, dispersed in the matrix, by performing steps of:

(a) acquiring a film thickness of the sample;

(b) acquiring an average density of the sample;

(c) acquiring the particle density;

(d) measuring a measured profile of a scattered X-ray intensity of the sample using X-ray small angle scattering measurement equipment;

(e) producing a theoretical profile of the scattered X-ray intensity of the sample using the acquired film thickness and the acquired average density;

(f) carrying out a parameter fitting operation between the measured profile of the scattered X-ray intensity measured by the X-ray small angle scattering measurement equipment and the theoretical profile of the scattered X-ray intensity, and calculating a scale factor of the scattered X-ray intensity;

(g) acquiring a known particle content of a first sample;

(h) calculating an equipment constant of the X-ray small angle scattering measurement equipment based on the known particle content of the first sample and a first scale factor calculated for the first sample;

(i) calculating a particle content of a second sample having an unknown particle content based on a second scale factor calculated for the second sample and the calculated equipment constant; and (h) generating a signal indicative of the calculated particle content.

5. A method for measuring a particle content of a sample which is made of a thin film having a matrix with a known matrix density and particles dispersed in the matrix comprising the steps of:

(a) preparing a first sample having a known particle content and a second sample having an unknown particle content;

(b) executing an X-ray reflectance measurement for the first sample to get a first reflectance profile and determining an average density and a film thickness of the first sample based on the first reflectance profile;

(c) executing an X-ray small angle scattering measurement for the first sample to get a first measured profile of a scattered X-ray intensity, and carrying out a parameter fitting operation between the first measured profile of the scattered X-ray intensity and a theoretical profile of the scattered X-ray intensity, which is calculated based on the average density, the film thickness and the matrix density of the first sample, to determine a first scale factor of the scattered X-ray intensity;

(d) calculating an equipment constant of an X-ray small angle scattering measurement equipment based on the first scale factor and the known particle content of the first sample;

(e) executing an X-ray reflectance measurement for the second sample to get a second reflectance profile and determining an average density and a film thickness of the second sample based on the second reflectance profile;

(f) executing an X-ray small angle scattering measurement for the second sample using the same X-ray small angle scattering measurement equipment as for the first sample to get a second measured profile of the scattered X-ray intensity, and carrying out a parameter fitting operation between the second measured profile of the scattered X-ray intensity and a theoretical profile of the scattered X-ray intensity, which is calculated based on the average density, the film thickness and the matrix density of the second sample, to determine a second scale factor of the scattered X-ray intensity;

(g) calculating a particle content of the second sample based on the equipment constant and the second scale factor; and (h) generating a signal indicative of the calculated particle content.

6. An method for measuring a particle content of a sample which is made of a thin film having a matrix with a known matrix density and particles dispersed in the matrix, by performing steps of:

(a) acquiring a film thickness of the sample;

(b) acquiring an average density of the sample;

(c) acquiring the matrix density;

(d) measuring a measured profile of a scattered X-ray intensity of the sample using X-ray small angle scattering measurement equipment;

(e) producing a theoretical profile of the scattered X-ray intensity of the sample using the acquired film thickness, the acquired average density and the acquired matrix density;

(f) carrying out a parameter fitting operation between the measured profile of the scattered X-ray intensity measured by the X-ray small angle scattering measurement equipment and the theoretical profile of the scattered X-ray intensity, and calculating a scale factor of the scattered X-ray intensity;

(g) acquiring a known particle content of a first sample;

(h) calculating an equipment constant of the X-ray small angle scattering measurement equipment based on the known particle content of the first sample and a first scale factor calculated for the first sample;

(i) calculating a particle content of a second sample having an unknown particle content based on a second scale factor calculated for the second sample and the calculated equipment constant; and (j) generating a signal indicative of the calculated particle content.

7. A method for measuring a void content of a sample which is made of a thin film having a matrix and voids dispersed in the matrix comprising the steps of:

(a) preparing a plurality of samples each of which has an unknown matrix density and an unknown void content, the unknown matrix densities of the samples being expected to be identical with each other whereas the unknown void contents of the samples being expected to be different from each other;

(b) executing, for each one of the samples, an X-ray reflectance measurement to get a reflectance profile and determining an average density and a film thickness of the sample based on the reflectance profile;

(c) executing, for each one of the samples, an X-ray small angle scattering measurement to get a measured profile of a scattered X-ray intensity, and carrying out, for each one of the samples, a parameter fitting operation between the measured profile of the scattered X-ray intensity and a theoretical profile of the scattered X-ray intensity, which is calculated based on the average density and the film thickness of the sample, to determine a scale factor of the scattered X-ray intensity for each one of the samples;

(d) calculating matrix densities of the samples based on the scale factors of the samples so that differences in the matrix densities among the samples become a minimum;

(e) calculating, for at least one of the samples, a void content of the sample based on the average density and the matrix density of the sample; and (h) generating a signal indicative of the calculated void content.

8. A method according to claim 7, wherein the plurality of the samples are at least three samples.

9. A method according to claim 7, wherein the step of calculating matrix densities includes the steps of:

selecting one of the samples as a reference sample;

expressing each of the matrix densities of the samples other than the reference sample by a formula including the average density and the scale factor of the sample in question and the average density, the scale factor and the matrix density of the reference sample;

determining the matrix density of the reference sample so that differences in the matrix densities among the samples become a minimum; and calculating matrix densities of the samples other than the reference sample based on the matrix density of the reference sample.

10. A method according to claim 9, wherein the plurality of the samples are at least three samples.

11. An method for measuring a void content of a sample which is made of a thin film having a matrix and voids dispersed in the matrix, by performing steps of:

(a) acquiring a film thickness of the sample;

(b) acquiring an average density of the sample;

(c) measuring a measured profile of a scattered X-ray intensity of the sample using X-ray small angle scattering measurement equipment;

(d) producing a theoretical profile of the scattered X-ray intensity of the sample using the acquired film thickness and the acquired average density;

(e) carrying out a parameter fitting operation between the measured profile of the scattered X-ray intensity measured by the X-ray small angle scattering measurement equipment and the theoretical profile of the scattered X-ray intensity, and calculating a scale factor of the scattered X-ray intensity;

(f) calculating matrix densities of the samples based on the calculated scale factors so that differences in the matrix densities among the samples become a minimum;

(g) calculating, for at least one of the samples, a void content based on the acquired average density and the calculated matrix density; and (h) generating a signal indicative of the calculated void content.

12. A method for measuring a particle content of a sample which is made of a thin film having a matrix and particles, with a known particle density, dispersed in the matrix comprising the steps of:

(a) preparing a plurality of samples each of which has an unknown matrix density and an unknown particle content, the unknown matrix densities of the samples being expected to be identical with each other whereas the unknown particle contents of the samples being expected to be different from each other;

(b) executing, for each one of the samples, an X-ray reflectance measurement to get a reflectance profile and determining an average density and a film thickness of the sample based on the reflectance profile;

(c) executing, for each one of the samples, an X-ray small angle scattering measurement to get a measured profile of a scattered X-ray intensity, and carrying out, for each one of the samples, a parameter fitting operation between the measured profile of the scattered X-ray intensity and a theoretical profile of the scattered X-ray intensity, which is calculated based on the average density, the film thickness and the particle density of the sample, to determine a scale factor of the scattered X-ray intensity for each one of the samples;

(d) calculating matrix densities of the samples based on the scale factors of the samples so that differences in the matrix densities among the samples become a minimum;

(e) calculating, for at least one of the samples, a particle content of the sample based on the particle density, the average density and the matrix density of the sample; and (h) generating a signal indicative of the calculated particle content.

13. A method according to claim 12, wherein the step of calculating matrix densities includes the steps of:

selecting one of the samples as a reference sample;

expressing each of the matrix densities of the samples other than the reference sample by a formula including the particle density, the average density and the scale factor of the sample in question and the particle density, the average density, the scale factor and the matrix density of the reference sample;

determining the matrix density of the reference sample so that differences in the matrix densities among the samples become a minimum; and calculating matrix densities of the samples other than the reference sample based on the matrix density of the reference sample.

14. An method for measuring a particle content of a sample which is made of a thin film having a matrix and particles, with a known particle density, dispersed in the matrix, by performing steps of:
- (a) acquiring a film thickness of the sample;
- (b) acquiring an average density of the sample;
- (c) acquiring the particle density;
- (d) measuring a measured profile of a scattered X-ray intensity of the sample using X-ray small angle scattering measurement equipment;
- (e) producing a theoretical profile of the scattered X-ray intensity of the sample using the acquired film thickness, the acquired average density and the acquired particle density;
- (f) carrying out a parameter fitting operation between the measured profile of the scattered X-ray intensity measured by the X-ray small angle scattering measurement equipment and the theoretical profile of the scattered X-ray intensity, and calculating a scale factor of the scattered X-ray intensity;
- (g) calculating matrix densities of the samples based on the scale factors calculated by the scalefactorcalculating means so that differences in the matrix densities among the samples become a minimum;
- (h) calculating, for at least one of the samples, a particle content based on the acquired average density, the acquired particle density and the calculated matrix density; and
- (h) generating a signal indicative of the calculated particle content.

15. A method for measuring a particle content of a sample which is made of a thin film having a matrix with a known matrix density and particles dispersed in the matrix comprising the steps of:
- (a) preparing a plurality of samples each of which has an unknown particle density and an unknown particle content, the unknown particle densities of the samples being expected to be identical with each other whereas the unknown particle contents of the samples being expected to be different from each other;
- (b) executing, for each one of the samples, an X-ray reflectance measurement to get a reflectance profile and determining an average density and a film thickness of the sample based on the reflectance profile;
- (c) executing, for each one of the samples, an X-ray small angle scattering measurement to get a measured profile of a scattered X-ray intensity, and carrying out, for each one of the samples, a parameter fitting operation between the measured profile of the scattered X-ray intensity and a theoretical profile of the scattered X-ray intensity, which is calculated based on the average density, the film thickness and the matrix density of the sample, to determine a scale factor of the scattered X-ray intensity for each one of the samples;
- (d) calculating particle densities of the samples based on the scale factors of the samples so that differences in the particle densities among the samples become a minimum;
- (e) calculating, for at least one of the samples, a particle content of the sample based on the matrix density, the average density and the particle density of the sample; and
- (h) generating a signal indicative of the calculated particle content.

16. An method for measuring a particle content of a sample which is made of a thin film having a matrix with a known matrix density and particles dispersed in the matrix, by performing steps of:
- (a) acquiring a film thickness of the sample;
- (b) acquiring an average density of the sample;
- (c) acquiring the matrix density;
- (d) measuring a measured profile of a scattered X-ray intensity of the sample using X-ray small angle scattering measurement equipment;
- (e) producing a theoretical profile of the scattered X-ray intensity of the sample using the acquired film thickness, the acquired average density and the acquired matrix density;
- (f) carrying out a parameter fitting operation between the measured profile of the scattered X-ray intensity measured by the X-ray small angle scattering measurement equipment and the theoretical profile of the scattered X-ray intensity, and calculating a scale factor of the scattered X-ray intensity;
- (g) calculating particle densities of the samples based on the scale factors calculated by the scalefactorcalculating means so that differences in the particle densities among the samples become a minimum;
- (h) calculating, for at least one of the samples, a particle content based on the acquired average density, the acquired matrix density and the calculated particle density; and
- (h) generating a signal indicative of the calculated particle content.

* * * * *